US007670791B1

(12) United States Patent
Shin et al.

(10) Patent No.: US 7,670,791 B1
(45) Date of Patent: Mar. 2, 2010

(54) METHOD FOR THE SUPPRESSION OF VISCERAL PAIN BY REGULATING T-TYPE CALCIUM CHANNEL

(75) Inventors: Hee-Sup Shin, Gyeonggi-do (KR); Dae-Soo Kim, Seoul (KR); Chan-Ki Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/753,108

(22) Filed: May 24, 2007

Related U.S. Application Data

(62) Division of application No. 10/284,889, filed on Oct. 31, 2002, now abandoned.

(30) Foreign Application Priority Data

Nov. 2, 2001 (KR) ............................. 2001/68180

(51) Int. Cl.
*G01N 33/53* (2006.01)
*G01N 33/566* (2006.01)
*G01N 33/567* (2006.01)
(52) U.S. Cl. .................. 435/7.2; 435/7.1; 435/7.21; 436/501; 424/9.1; 514/2
(58) Field of Classification Search ................. None
See application file for complete search history.

(56) References Cited

U.S. PATENT DOCUMENTS

| 4,808,605 | A | 2/1989 | Branca et al. | |
| 5,773,462 | A | 6/1998 | Harling et al. | |
| 6,309,858 | B1 * | 10/2001 | Dietrich et al. | ............ 435/69.1 |

FOREIGN PATENT DOCUMENTS

| WO | 99/28342 Y | 6/1999 |
| WO | 01/30844 Y | 5/2001 |

OTHER PUBLICATIONS

Del Pozo et al. (1987). Analgesic effects of several calcium channel blockers in mice. European Journal of Pharmacology. 137:155-160.*
Farkas, Andras, et al., Inadequate Ischaemia-Selectivity Limits the Antiarrhythmic . . . , British Journal of Pharmacology, vol. 128, pp. 41-50, 1999.
Talley, Edmund M. et al., Differential Distribution of Three Members of a Gene Family . . . , The Journal of Neuroscience, vol. 19, pp. 1895-1911, 1999.
Kim, Daesoo, et al., Thalamic Control of Visceral . . . , Science, vol. 302, pp. 117-119, 2003.
Cannon, Richard O., et al., Imipramine in Patients With Chest Pain . . . , The New England Journal of Medine, vol. 330, pp. 1411-1417, 1994.
Mukherjee, R. and Spinale, F.G., L-Type Calcium Channel Abundance and Function . . . , J. Mol. Cell Cardiol., vol. 30, pp. 1899-1916, 1998 (Pub Med Abstract).
Massie, B.M., Mibefradil, A T-Type Channel-Selective Calcium Antagonist . . . , Am. J. Hypertens., vol. 11, pp. 95S-102S, 1998, (Pub Med Abstract).
Nehme, O.S. and Rogers, A.I., New Developments in Colonic Ischemia, Curr. Gastroenterol. Rep., vol. 3, pp. 416-419, 2001 (Pub Med Abstract).
Barsky, A.J., et al., Silent Myocardial Ischemia . . . , JAMA, vol. 264, pp. 1132-1135, 1991 (Pub Med Abstract).
La, Jun-Ho, et al., Visceral Hypersensitivity and Altered Colonic Motility . . . , World J. Gastroenterol, vol. 9, pp. 2791-2795, 2003.
Striessnig, Jorg, Pharmacology, Structure . . . , Cell Physiol . Biochem., vol. 9, pp. 242-269, 1999.
Daesoo Kim, Lack of the Burst Firing of Thalamocortical Relay Neurons . . . , vol. 31, pp. 35-45, 2001.
Vikaas S. Sohal, et al., It Takes T to Tango, Neuron, vol. 31, pp. 3-7, 2001.
Harford, The Syndrome of Angina Pectoris: Role of Visceral Pain Perception, American Journal of Medical Science, vol. 307, No. 4, pp. 305-315, 1994.
Bennet, et al., Cecil Textbook of Medicine, 20th edition, pp. 715-721, 1996.
The Merck Manual, Fifteenth edition, pp. 751.
Matthews, Elizabeth, et al., Effects of Ethosuximide, A T_Type Ca2 . . . , European Journal of Pharmacology, vol. 415, No. 2-3, pp. 141-149, (2001) XP002430083.
Todorovic, Slobodan M., et al., Mechanical and Thermal Antinociception in Rats . . . , Brain Research, vol. 951, No. 2, pp. 336-340, (2002) XP002430084.
Muth, J. N., et al., Use of Transgenic Mice to Study . . . , Trends in Pharmacological Sciences . . . , vol. 22, No. 10, pp. 526-532, (2001) XP004307622.
Ding, Yaoxian, et al., Nifedipine and Diltiazem But Not Verapamil . . . , vol. 292, No. 2, The Journal of Pharmacology, etc., pp. 6060-6609, 2000.
Dessy, Chantal, et al., The Effect of L-Type Calcium Channel Modulators . . . , vol. 119, pp. 142-148, 1996.
Jinnah, H. A., et al., Calcium Channel Activation and Self-Biting . . . , PNAS, vol. 95, No. 26, pp. 15228-15232, 1999.
Oroko, J. Pharm. Pharmcol., vol. 51, No. 8, pp. 953-957, 1999.
Kim, Daesoo, et al., Thalamic Control of Visceral . . . , vol. 302, pp. 117-119, 2003.

* cited by examiner

*Primary Examiner*—Christine J Saoud
*Assistant Examiner*—Jon M Lockard
(74) *Attorney, Agent, or Firm*—Lucas & Mercanti, LLP

(57) ABSTRACT

The disclosure concerns a method for the suppression of visceral pain by regulating the T-type calcium channel; a visceral pain inhibitor that includes a T-type calcium channel inhibitor as an effective ingredient; and a method of screening a visceral pain inhibitor by investigating the suppression activity of T-type calcium channels. Particularly, the present invention relates to a method for the suppression of visceral pain by regulating an alpha 1G T-type calcium channel in the central nervous system and alpha 1H and alpha 1I T-type calcium channels in the peripheral nervous system; a visceral pain inhibitor that includes a T-type calcium channel inhibitor as an effective ingredient; and a method of screening a visceral pain inhibitor by investigating the suppression activity of T-type calcium channels. The method of the present invention can be effectively used to suppress visceral pain by regulating T-type calcium channel in a precise mechanism without any side effects.

4 Claims, 4 Drawing Sheets

METHOD FOR THE SUPPRESSION OF VISCERAL PAIN BY REGULATING T-TYPE CALCIUM CHANNEL

CROSS-REFERENCE TO RELATED APPLICATIONS

This patent application is a divisional of U.S. patent application Ser. No. 10/284,889 filed Oct. 31, 2002, now abandoned, which claims a benefit of priority from Korean Patent Application No. 2001/68180 filed Nov. 2, 2001, the contents of each of which are incorporated herein by reference herein in its entirety.

FIELD OF THE INVENTION

The present invention relates to a method for the suppression of visceral pain by regulating the T-type calcium channel; a visceral pain inhibitor that includes a T-type calcium channel inhibitor as an effective ingredient; and a method of screening a visceral pain inhibitor by investigating the suppression activity of T-type calcium channels. Particularly, the present invention relates to a method for the suppression of visceral pain by regulating an alpha 1G T-type calcium channel in the central nervous system and alpha 1H and alpha 1I T-type calcium channels in the peripheral nervous system; a visceral pain inhibitor that includes a T-type calcium channel inhibitor as an effective ingredient; and a method of screening a visceral pain inhibitor by investigating the suppression activity of T-type calcium channels.

BACKGROUND OF THE INVENTION

Visceral pain is usually caused by excessive dilation of internal organs, necrosis of these cells or intensive contraction or acute relaxation of internal organs. When there is a tumor, infection or congestion in internal organs, slight mechanical stimulus, acidic or basic solution might cause severe pain. Visceral pain caused especially by tumors cannot be easily suppressed even with an excessive amount of morphine, so neuro-surgical operations such as partial myelotomy of the spinal cord are frequently used (Gybels, *Pain Headache*, 1989, 11:1-402). However, the bilateral cordotomies or commissural myelotomies of spinothalamic tract have many side effects. Relatively, the midline myelotomy that severs the upper middle part of the T10 spinal cord is known as an effective remedy (Nauta, *J. Neurosurg.*, 1997, 86:538-542).

The above result proves that the visceral pain signal is delivered to the brain through the spinal cord, which supports the fact that the visceral pain signal is delivered through a different channel from other pains. According to a MRI test carried out on a-visceral-pain-induced monkey, it can be known that visceral pain induces the activation of thalamus (Willis, *Proc. Natl. Acad. Sci. USA.*, 1999, 96:7675-79). The result of the test, after all, tells that the visceral pain is delivered from the pain sensory cells in the end of the internal organs through the spinal cord to thalamus. Particularly, thalamus is known as an important sensory processing organ since it delivers the stimulus to the cerebral cortex (McCormick, *Curr. Opin. Neurobiol.*, 1994, 4:550-556).

The calcium in nerve cells plays an important role in delivering signals between nerve cells. Calcium has many different delivery paths, however, when delivering peripheral stimuli, the voltage-activated calcium channel is crucial. The voltage-activated calcium channel can be categorized into the high voltage-activated calcium channel (HVA) that is activated at a higher voltage than the resting membrane potential and the low voltage-activated calcium channel (LVA) that is activated at a lower voltage. The HVA calcium channel can be subdivided into L, P/Q, N or R-type depending on the pharmacological property of the current, and the LVA calcium channel is differentiated as T-type (Tsien, *Trends Neurosci.*, 1988, 11:431-438).

The HVA calcium channel is evenly expressed from the peripheral sensory cells to the central nervous system, and is well known to play an important role in transmission of the sense of pain and reflection. The inhibitors against these channels are already commercially available as various anodynes (Schaible, *Prog. Brain Res.*, 2000, 129:173-190). However, it is not yet clearly understood how the LVA calcium channel that generates the T-type calcium current can regulate pain. The reason why the T-type calcium current is categorized as one of the functions of the LVA calcium channel is that when the excitability of nerve cells lowers, the calcium current are generated so that the excitability increases again (Llinas, *J. Physiol (Lond)*, 1981, 315:549-567; McCormick, *Neuroscience*, 1990, 39:103-113). Thus, the nerve cells excited by the T-type calcium channel have the property of burst firings and induce a type of excitability different from tonic firings (Llinas, *J. Physiol (Lond)*, 1981, 315:549-567). The channel protein of the T-type calcium channel is encoded by three different genes, which are referred to as alpha1G, alpha1H and alpha1I respectively (Perez-Reyes, *Nature*, 1998, 391:896-900). It is known that the alpha1G and alpha1H T-type calcium channels are expressed in the back of the spinal cord, and that the alpha1G is expressed in thalamo-cortical relay neurons (Talley, *J. Neurosci.*, 1999, 19:1895-1911), and that is identical with the delivery path of the visceral pain. Recently, it has been proved in an experiment using a T-type calcium current inhibitor, mibefradil, that the function of the T-type calcium current in the peripheral nerves is related to hyperalgesic reaction against thermo-stimuli or mechanical stimuli by reducing agents (Todorovic, *Neuron*, 2001, 31:75-85), however, it has not yet been found which T-type calcium channel is related. Mibefradil (RO40-5967) was initially known for lowering blood pressure (Clozel, *Cardiovasc Drugs Ther.*, 1990, 4:731-736; Hefti, *Arzneimittelforschung*, 1990, 40:417-421), and was reported to have a suppression effect (Viana, *Cell Calcium*, 1997, 22:299-311). Recently, it has been reported that Mibetradil has the most selective suppression effect on T-type calcium channels.

Thus, the present inventors have studied about visceral pain with alpha1G−/− transgenic mice and found that the alpha1G−/− transgenic mice show hyperalgesia to visceral pain caused by acetic acid. In wild-type mice, visceral pain caused by acetic acid could be alleviated by administration of mibefradil at the periphery but enhanced when mibefradil is injected in the brain. The present invention has been accomplished by confirming that visceral pain can be modulated by controlling the T-type calcium channel.

SUMMARY OF THE INVENTION

It is an object of the present invention to provide a method for the suppression of visceral pain by regulating the T-type calcium channel.

It is another object of the present invention to provide a visceral pain inhibitor that includes a T-type calcium channel inhibitor as an effective ingredient.

It is a further object of the present invention to provide a method of screening a visceral pain inhibitor by investigating the suppression activity of T-type calcium channels.

DETAILED DESCRIPTION OF PREFERRED EMBODIMENTS

The present invention provides a method for the suppression of visceral pain by regulating the T-type calcium channel.

The present invention also provides a visceral pain inhibitor that includes a T-type calcium channel inhibitor as an effective ingredient.

The present invention also provides a method of screening a visceral pain inhibitor by investigating the suppression activity of T-type calcium channels.

Hereinafter, the present invention is described in detail.

The present invention provides a method for the suppression of visceral pain by regulating the T-type calcium channel.

The present invention provides a method for the suppression of visceral pain either by activating alpha 1G T-type calcium channel function in the brain or by suppressing alpha 1H and alpha 1I T-type calcium channel function in the peripheral nervous system.

The T-type calcium channel is categorized into alpha 1G, alpha 1H and alpha 1I depending on the organization unit of small-pore forming, and in the present invention, the inventors carried out an experiment related to pain by using the alpha 1G−/− transgenic mice so as to suppress the function of the alpha 1G protein, one of the component of alpha 1G T-type calcium channel. It has been known that mechanical stimuli, which are acute pains, are controlled by spinal reflex, and the responsiveness of the mechanical stimuli is proportionate with the intensity of the pains received by the peripheral organs. The alpha 1G−/− mice do not have much difference from the normal mice in the paw withdrawal and tail flick test (see FIG. 1). In addition, the result of the thermal pain response analysis using radiant heat in which spinal reflex and supraspinal mechanism is involved shows that the alpha 1G−/− mice does not have much difference from the normal mice, either in thermo-stimulus hyperalgesia caused by inflammation reaction or thermo-stimulus by infrared radiation (see FIG. 2). As mentioned above, deducing from the fact that the alpha 1G−/− mice reacts normally to thermal or mechanical stimuli, it can be known that the loss of the alpha 1G T-type calcium channel do not affect the development of the peripheral sensory organs, that is, the nerves that are involved in spinal reflection and inflammation reaction.

Figure 3:
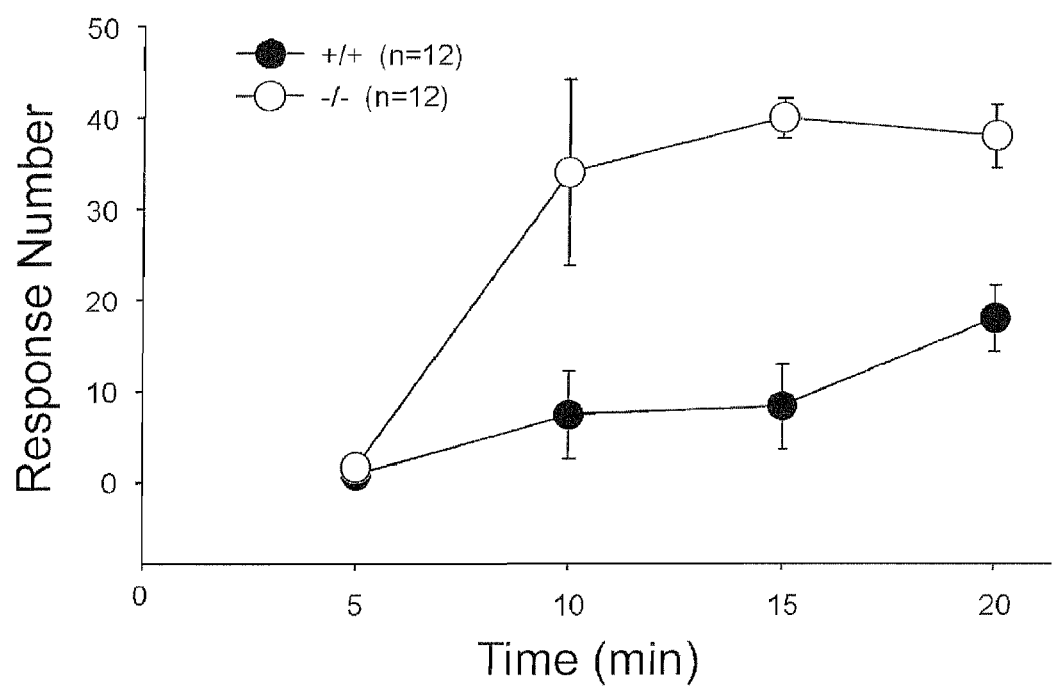
FIG. 3 is a graph showing the responses of alpha 1G−/− mice and normal mice against pain in internal organs that is caused by acetic acid,
●: normal mice ○: alpha 1G−/− mice

From the observation of the response of the internal pains induced by acetic acid, the alpha 1G−/− mice show serious hyperalgesia to the visceral pain induced by acetic acid (see FIG. 3). It shows that the alpha 1G T-type calcium channel is selectively involved in the control of visceral pain. In order to find out whether the alpha 1G T-type calcium channel that is involved in visceral pain control functions in the peripheral sensory organs or in the part where the spine is connected to the brain and thalamus, the present inventors injected mibefradil, a T-type inhibitor, in the same spot of acetic acid injection. The result was that there was analgesia to the visceral pain caused by the acetic acid (see FIG. 4). Mibefradil in this case suppresses the T-type calcium channel only in the peripheral nervous system since it cannot pass through the brain barrier inside the body.

From the result, it can be deduced that the pain suppression of the alpha 1G T-type calcium channel only functions in the central nervous system, not in the peripheral nervous system. It can also be known that the other types of the T-type calcium channels, alpha 1H and alpha 1T calcium channels increase pain in the peripheral nervous system.

As described above, the T-type calcium channel functions wholly differently in the peripheral nervous system and in the central nervous system concerning visceral pain control, and the T-type calcium channel is activated when the resting membrane potential lowers, thus suppressing the membrane potential from being low, which increase the activity of the visceral pain sensory cells in the peripheral organs. This is supported by the fact that the T-type calcium channel functions against hyperalgesia to mechanical or thermal stimuli induced by reducing agents. As for visceral pain, the dilation of intestinal cells or outflow of reduced substrates from cells caused by necrosis is brought along, so it is highly likely that hyperalgesia is already included in the normal algesia.

The present invention also provides a visceral pain inhibitor that includes a T-type calcium channel inhibitor as an effective ingredient.

When a visceral pain inhibitor that includes a T-type calcium channel inhibitor as an effective ingredient is injected into a body, the inhibitor reacts with alpha 1H and alpha 1I T-type calcium channel, which will eventually suppress visceral pain by suppressing the functions of the above-mentioned alpha 1H and alpha 1I T-type calcium channel.

In the present invention, the T-type calcium channel inhibitor is selected from a group consisting of mibefradil and $Ni^{2+}$.

Moreover, the present invention provides a method of screening a visceral pain inhibitor by investigating the suppression activation of the T-type calcium channel.

In the present invention, the suppression activity of the T-type calcium channel of chemical materials or natural materials is investigated; the materials that have suppression activity to the T-type calcium channel are selected; and among the selected materials, the material that has an analegesic effect only on the visceral pain induced by acetic acid, et al. is found by carrying out experiments related pain with alpha 1G−/− mice and normal mice.

In accordance with the present invention, the T-type calcium channel inhibitor has a suppression effect on visceral pain in a precise mechanism without any side effects, therefore, the selected material from these T-type calcium channel inhibitors can be used as a visceral pain inhibitor.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Generation and Management of Alpha 1G−/− Transgenic Mice

<1-1> Generation of Alpha 1G −/− Transgenic Mice

The present inventors have produced transgenic mice that have the genotype of alpha 1G−/− by using an embryo that has the genotype of alpha 1G+/− (International Depository Authority: Korea Institute of Bioscience and Biotechnology Gene Bank, Accession No: KCTC 10086 BP). Particularly, the heterozygote transgenic mice having alpha 1G−/− genotype was produced by transplanting the embryo having alpha 1G+/− genotype to a surrogate mother, and the homozygote transgenic mice having alpha 1G−/− genotype was produced by crossbreeding male and female of the above heterozygote transgenic mice.

<1-2> Management of Animal

All animals were allowed to access freely to food and water under the environment of controlled temperature and humidity, and they were bred under the condition in which the daytime starts at 8 of clock in a 12 hour cycle of daytime and nighttime. All male and female F2 mice were used in the experiments when they are 8-15 week old.

Example 2

Analysis of the Response to Mechanical Stimuli

In order to observe the response of the alpha 1G−/− mice to mechanical stimuli, the present inventors carried out a paw withdrawal test and a tail flick test.

<2-1> Paw Withdrawal Test

Paw withdrawal test was based on that described by Mogil et al (Mogil et al., *J. Neurosci.*, 1999, 19:RC25). Particularly, the alpha 1G −/− mice were placed individually on a fine mesh metal floor and allowed to acclimate for at least 2 hr. The mechanical threshold was measured using calibrated von Frey filaments (Stoelting) and was defined as the bending force, in grams, at which the mice withdraws its paw. The filament was applied from underneath the floor, through the mesh, to the plantar surface of the paw for each limb. The response score was assessed as the total numbers of paw withdrawals in 10 consecutive trials for each filament and the average value of the response was used in the analysis.

<2-2> Tail Flick Test

The local pressure required to elicit tail flick was determined using von Frey filaments. The alpha 1G −/− mice were habituated in the mice restrainer 30 minutes every day for 2 weeks. The bending force of each monofilament was applied locally to the tail resting on a table. Only flicking of the pressed tail was defined as a nociceptive response. The response score was assessed as the average of the total tail flicking number in 10 consecutive trials with an interval of 10 min between each filament application.

Figure 1:
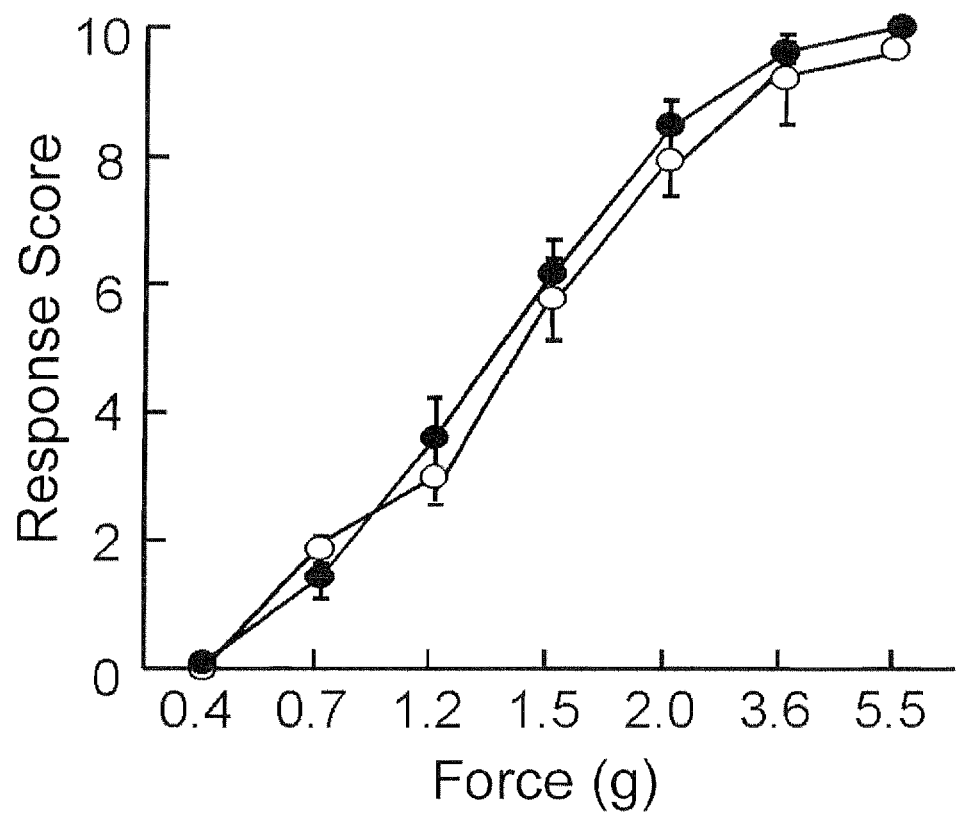
FIG. 1 is a graph showing the responses of alpha 1G−/− mice and normal mice against mechanical stimuli such as paw withdrawal and tail flick test;
●: normal mice ○: alpha 1G−/− mice

As a result, the alpha 1G −/− mice do not have any difference from the normal mice in responding to thermal or mechanical stimuli using von Frey (FIG. 1)

Example 3

Responses to Radiant Heat and Hot Plate

The present inventors examined the thermal pain response by using radiant heat assay (Hargreaves test) wherein the mechanism of spinal reflex and supraspine is involved.

<3-1> Paw Withdrawal Test

The present inventors measured hind-paw withdrawal latency by Hargreaves' method (Hargreaves et al., *Pain*, 1988, 32:77-88) using an Ugo Basile plantar test apparatus (Stoelting). Mice were placed in a Plexiglas box on an elevated glass plate and acclimated for 2 hr before testing. The tests were performed at low (20) and high (40) intensities. Response was defined as withdrawal of a paw when head turning and paw licking were observed. The time was defined as the paw withdrawal latency. Five to ten minutes were allowed between each trial on both hind-paws and 4 to 5 trials were averaged for each mice.

<3-2> Hot Plate Test

Thermal pain response was assessed using the hot-plate test (Mogil et al., *J. Neurosci.*, 1999, 19:RC25). For the hot-plate test, the mice was habituated for 2 days in a transparent testing box (14×14×20 cm) with a metal bottom. The mice was then placed on the box pre-heated to the desired temperature in a thermo-regulated water bath, and the time was recorded to the first hind-paw licking or jumping response (cut-off time, 60 s).

Figure 2:
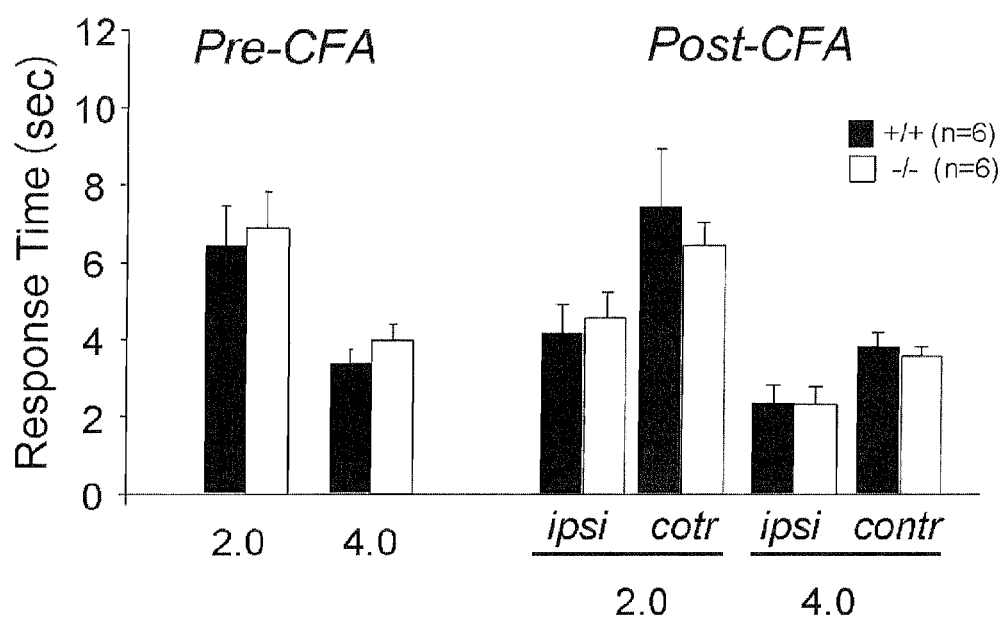
FIG. 2 is a graph showing the responses of alpha 1G−/− mice and normal mice against thermostimulus Hyperalgesia that is caused by a thermostimulus by radiation or by inflammation,
|: normal mice □: alpha 1G−/− mice

As a result, the alpha 1G −/− mice did not have much difference from the normal mice in the response to thermal hyperalgesia caused by inflammation reaction or thermo-stimuli by infrared radiation (FIG. 2). Thus, it was confirmed that the loss of the alpha 1G T-type calcium channel did not affect the development of the peripheral sensory organs, that is, the nerves that are involved in spinal reflection and inflammation reaction.

Example 4

Analysis of Visceral Pain Induced by Acetic Acid (Writhing Test)

The present inventors injected 0.6% acetic acid into the peritoneal cavity of mice to examine the acetic acid-induced visceral pain response. The visceral pain is elicited secondarily to a delayed inflammatory response and induced abdominal stretching and writhing behavior (Gyires and Torma, *Arch Int. Pharmacodyn. Ther.*, 1984, 267:131-140). Mice were placed individually in a transparent home cage (24×18×12 cm) and allowed to acclimate for at least 60 min. Then, 0.6% acetic acid (5.0 mg/kg) was injected into the peritoneum, after which the mice was returned to the testing chamber. The number of abdominal stretches or writhing motions was counted for 20 min. All mice were used only once in this experiment.

As a result, the alpha 1G −/− mice showed severe hyperalgesia to the visceral pain induced by acetic acid (FIG. 3), which means that the alpha 1G T-type calcium channel is involved selectively in controlling the sense of visceral pain.

Example 5

Analysis of Visceral Pain Induced by Mibefradil

In order to find where the alpha 1G T-type calcium channel functions in relation to controlling visceral pain, whether the peripheral nerves or the part where the spine was connected to thalamus and brain, the T-type inhibitor, mibefradil, was injected into peritoneum, the same spot where the acetic acid (the visceral pain inducer for the normal mice) was injected.

Particularly, in order to find out how mibefradil, the T-type calcium channel inhibitor functions, mibefreail was dissolved in 0.9% of NaCl at the concentration of 5 mg/ml. The degree of writhing was measured in a visceral pain inducing experiment 20 minutes after the injection of the said mibefradil at the concentration of 1, 10 and 30 mg/kg respectively in peritoneum of the mice.

Figure 4:
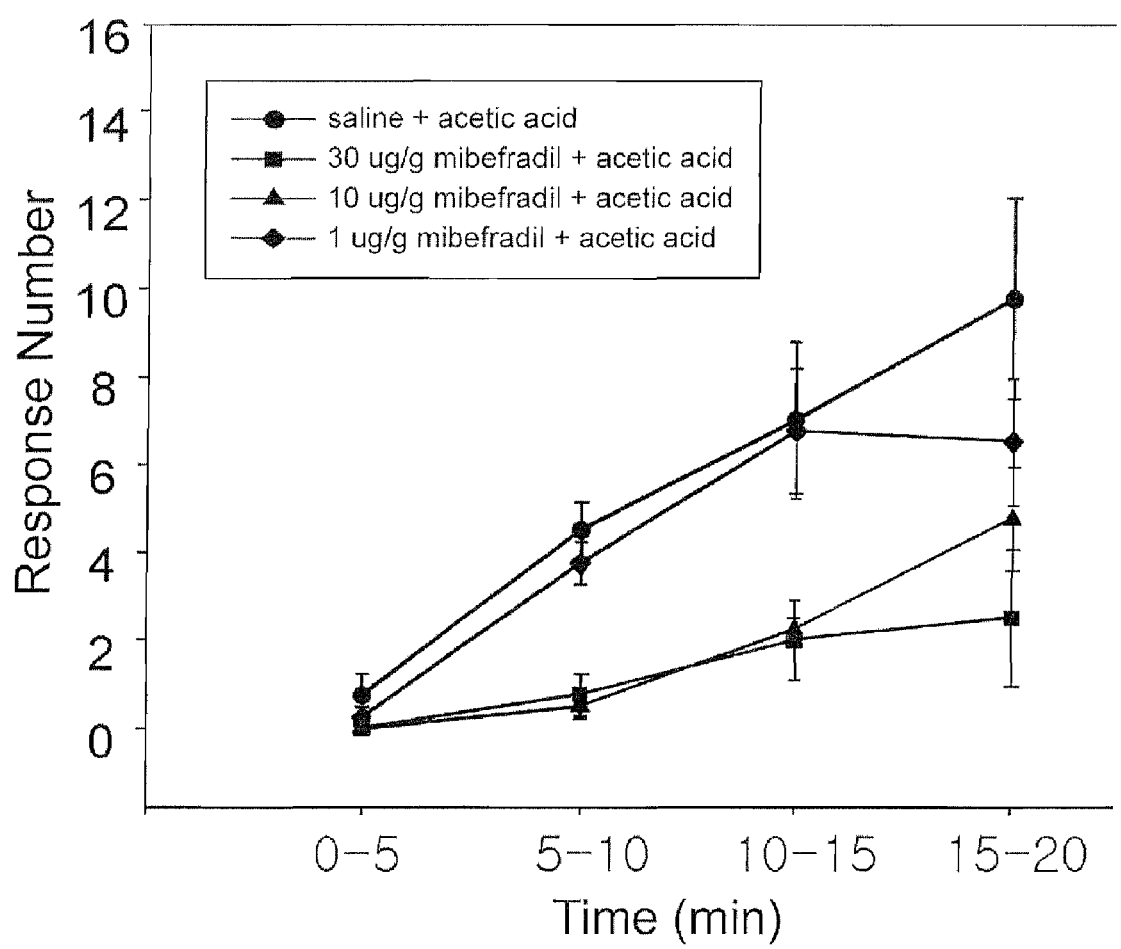
FIG. 4 is a graph showing the suppression degree in accordance with the concentration of a T-type calcium channel inhibitor, mibefradil.

As a result, the mibefradil induced analgesia to the visceral pain caused by acetic acid in the normal mice (FIG. 4).

INDUSTRIAL APPLICABILITY

As shown above, a method of the present invention can be effectively used to suppress visceral pain by regulating T-type calcium channel in a precise mechanism without any side effects.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of identifying a material that is a visceral pain inhibitor comprising:
    (a) screening whether chemical materials or natural material suppress T-type calcium channel activity;
    (b) selecting the materials among the chemical materials or natural material screened in step (a) which suppress activity of T-type calcium channel; and
    (c) determining whether the materials selected in step (b) has an analegesic effect on the visceral pain of an animal.

2. The method according to claim 1, wherein the analgesic effect on the visceral pain is identified by counting the number of abdominal stretches or writhing motions of an animal whose visceral pain is induced by acetic acid.

3. The method according to claim 1, wherein the animal is a mouse.

4. The method according to claim 2, wherein the animal is a mouse.

* * * * *